US011667696B2

(12) United States Patent
Meyer

(10) Patent No.: US 11,667,696 B2
(45) Date of Patent: Jun. 6, 2023

(54) SELECTIVE REDUCTION OF PROTEINS

(71) Applicant: Seagen Inc., Bothell, WA (US)

(72) Inventor: Damon L. Meyer, Bellevue, WA (US)

(73) Assignee: Seagen Inc., Bothell, WA (US)

(*) Notice: Subject to any disclaimer, the term of this patent is extended or adjusted under 35 U.S.C. 154(b) by 313 days.

(21) Appl. No.: 16/580,290

(22) Filed: Sep. 24, 2019

(65) Prior Publication Data

US 2020/0115438 A1 Apr. 16, 2020

Related U.S. Application Data

(62) Division of application No. 15/117,254, filed as application No. PCT/US2015/015369 on Feb. 11, 2015, now Pat. No. 10,464,997.

(60) Provisional application No. 61/938,378, filed on Feb. 11, 2014.

(51) Int. Cl.
C07K 16/00 (2006.01)
A61K 47/68 (2017.01)
C07K 1/36 (2006.01)
C07K 1/08 (2006.01)
C07K 1/113 (2006.01)

(52) U.S. Cl.
CPC .............. C07K 16/00 (2013.01); A61K 47/68 (2017.08); A61K 47/6817 (2017.08); A61K 47/6889 (2017.08); C07K 1/086 (2013.01); C07K 1/1133 (2013.01); C07K 1/36 (2013.01); C07K 2317/52 (2013.01); C07K 2317/53 (2013.01)

(58) Field of Classification Search
CPC ...... C07K 16/00; C07K 1/086; C07K 1/1133; C07K 1/36; C07K 2317/52; C07K 2317/53; A61K 47/48; A61K 47/6889; A61K 47/6817
USPC ...................................................... 530/388.1
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 5,219,996 A | 6/1993 | Bodmer et al. | |
| 5,585,089 A | 12/1996 | Queen et al. | |
| 5,939,598 A | 8/1999 | Kucherlapati et al. | |
| 6,111,166 A | 8/2000 | Van de Winkel | |
| 6,130,237 A | 10/2000 | Denny et al. | |
| 6,884,869 B2 | 4/2005 | Senter et al. | |
| 7,498,298 B2 | 3/2009 | Doronina et al. | |
| 7,659,241 B2 | 2/2010 | Senter et al. | |
| 8,343,928 B2 | 1/2013 | Doronina et al. | |
| 8,609,105 B2 | 12/2013 | Senter et al. | |
| 10,464,997 B2 | 11/2019 | Meyer | |
| 2003/0083263 A1 | 5/2003 | Doronina et al. | |
| 2003/0105017 A1 | 6/2003 | Conn et al. | |
| 2006/0024317 A1 | 2/2006 | Boyd et al. | |
| 2009/0111756 A1 | 4/2009 | Doronina et al. | |
| 2011/0033378 A1 | 2/2011 | Dimasi et al. | |
| 2013/0330350 A1 | 12/2013 | Dimasi | |

FOREIGN PATENT DOCUMENTS

| | | |
|---|---|---|
| CN | 101212984 A | 7/2008 |
| WO | 96/14339 A1 | 5/1996 |
| WO | 02/088172 A2 | 11/2002 |
| WO | 02/088172 A3 | 11/2002 |
| WO | 2004/010957 A2 | 2/2004 |
| WO | 2004/010957 A3 | 2/2004 |
| WO | WO 2006/034488 | 3/2006 |
| WO | 2006/113909 A2 | 10/2006 |
| WO | 2006/113909 A3 | 10/2006 |
| WO | 2006/134173 A2 | 12/2006 |
| WO | 2007/003898 A1 | 1/2007 |
| WO | 2007/085930 A1 | 8/2007 |
| WO | 2008/025020 A2 | 2/2008 |
| WO | 2008/025020 A3 | 2/2008 |
| WO | 2009/052431 A2 | 4/2009 |
| WO | 2009/052431 A3 | 4/2009 |
| WO | 2009/092011 A1 | 7/2009 |
| WO | 2009/092011 A8 | 7/2009 |
| WO | 2010/091150 A1 | 8/2010 |
| WO | 2011/023883 A1 | 3/2011 |
| WO | 2011/061492 A2 | 5/2011 |
| WO | 2011/061492 A3 | 5/2011 |
| WO | 2012/112708 A1 | 8/2012 |

(Continued)

OTHER PUBLICATIONS

International Search Report and Written Opinion corresponding to PCT/US2015/015369 dated May 15, 2015, 3 pages.
Extended European Search Report corresponding to EP 15749202.6 dated Aug. 28, 2017, 6 pages.
Chari, Ravi V. J et al., "Immunoconjugates Containing Novel Maytansinoids: Promising Anticancer Drugs," *Cancer Research* (Jan. 1, 1992); 52:127-131.
Fraczkiewicz, Robert et al., "Exact and Efficient Analytical Calculation of the Accessible Surface Areas and Their Gradients for Macromolecules," *Journal of Computational Chemistry* (1998; accepted Sep. 2, 1997); 19(3):319-333.

(Continued)

*Primary Examiner* — Yan Xiao
(74) *Attorney, Agent, or Firm* — Fish & Richardson P.C.

(57) ABSTRACT

The present invention provides a method for making uncapped cysteine protein preparations, including uncapped engineered cysteine antibody preparations. The methods include, inter alia, contacting a reducing agent with engineered cysteine antibody molecules, each of the antibody molecules having at least one capped engineered cysteine residue and at least one interchain disulfide bond and reacting the reducing agent with the antibody molecules under conditions sufficient to uncap engineered cysteine residues and form cap byproducts. The method also includes removing the cap byproduct during the reduction reaction. Substantially all of the interchain disulfide bonds present in the antibody molecules prior to reduction are retained following reduction. Antibody conjugates and methods for preparing antibody conjugates using uncapped antibody preparations are also described.

14 Claims, 5 Drawing Sheets

(56) References Cited

FOREIGN PATENT DOCUMENTS

WO   2013/173496 A2   11/2013
WO   2013/173496 A3   11/2013

OTHER PUBLICATIONS

Frankel, Arthur E. et al., "Cell Surface Receptor-Targeted Therapy of Acute Myeloid Leukemia: A Review," *Cancer Biotherapy & Radiopharmaceuticals* (2000); 15(5):459-476.

Junutula, Jagath R. et al., "Site-specific conjugation of a cytotoxic drug to an antibody improves the therapeutic index," *Nature Biotechnology* (Aug. 2008; pub online Jul. 20, 2008); 26(8):925-932.

Murray, James L., "Monoclonal Antibody Treatment of Solid Tumors: A Coming of Age," *Seminars in Oncology* (Dec. 2000); 27(6) Suppl 11:64-70.

SELECTIVE REDUCTION OF PROTEINS

CROSS-REFERENCES TO RELATED APPLICATIONS

This application is a divisional of U.S. patent application Ser. No. 15/117,254 filed Aug. 8, 2016 which is a U.S. 371 National Stage Application of International Application No. PCT/US2015/015369 filed Feb. 11, 2015, which application claims priority to U.S. Application Ser. No. 61/938,378 filed Feb. 11, 2014, each of which is incorporated herein by reference in its entirety.

BACKGROUND OF THE INVENTION

Monoclonal antibodies in which selected amino acids have been mutated to cysteine (i.e., engineered cysteine mAbs, or ecmAbs) are particularly suitable for use in conjugates (e.g., antibody drug conjugates (ADCs)) because the conjugates derived from them can have favorable properties including homogeneity, favorable pharmacokinetics, stability, and solubility. The cysteine mutations are placed in locations in the amino acid sequence of the antibody which generally do not form inter- or intra-chain disulfide bonds, and expression machinery inside the cell producing the mutant mAb treats the cysteine residues as unpaired cysteines. Consequently, the engineered cysteines are generally expressed in the form of mixed disulfides with non-encoded cysteine molecules (i.e., the engineered cysteines are "capped" with capping agents, e.g., cysteine, cysteinyl glycine, or glutathione).

Hence, in order to prepare conjugates (e.g., ADC) from ecmAbs, it is generally necessary to subject the ecmAb to reducing conditions to convert the engineered cysteine from a mixed disulfide to a free thiol, and typically this uncapping or "activation" is accompanied by reduction of the ecmAb inter-chain disulfides. Although inter-chain disulfides can be re-formed by mild oxidation, such re-oxidation steps add to the complexity and expense of ADC preparation. Selective reduction methods have been elusive, as it has proven difficult to reduce the engineered cysteines without simultaneously reducing the inter-chain disulfides. Consequently, selective reduction methods for uncapping of engineered cysteine residues are needed. The present invention addresses this and other needs.

BRIEF SUMMARY OF THE INVENTION

The invention provides, inter alia, a method for selectively reducing engineered cysteine antibodies. The method includes contacting a reducing agent with engineered cysteine antibody molecules, each of the antibody molecules having at least one capped engineered cysteine residue and at least one inter-chain disulfide bond, and reacting the reducing agent with the antibody molecules under conditions sufficient to uncap engineered cysteine residues and form cap byproducts. Cap byproduct is removed during the reduction reaction. The methods result in the formation of an uncapped engineered cysteine antibody preparation. The uncapped engineered cysteine antibody preparation can contain both capped and uncapped engineered cysteine antibody. Substantially all of the inter-chain disulfide bonds present in the antibody molecules prior to the reduction reaction are retained in the uncapped engineered cysteine antibody preparation. The method can further comprise the step of supplementing the reduction reaction with additional reducing agent while removing cap byproduct. Removing the cap byproduct from the reaction mixture during the reduction reaction can be, for example, via dialysis or diafiltration. In preferred embodiments, the concentration of the cap byproduct is maintained in the reduction reaction mixture below the concentration at which re-capping prevents further activation of engineered cysteine residues In some aspects, the methods provide an uncapped engineered cysteine antibody preparation. Typically, at least about 60% of the engineered cysteine residues present in the antibody preparation are uncapped engineered cysteine residues. In some aspects, at least about 70%, at least about 75% or at least about 80% of the engineered cysteine residues present in the antibody preparation are uncapped engineered cysteine residues. In some aspects, using the present methods, at least 85% of the inter-chain disulfide bonds present in the antibody molecules prior to the reduction reaction are retained in the uncapped engineered cysteine antibody preparation. In some aspects, the reducing agent and reducing conditions are selected such that no more than about 20%, no more than about 15%, no more than about 10% or no more than about 5% of the inter-chain disulfide bonds present in the antibody molecules are converted during the reduction reaction to a pair of free thiols.

In related aspects, the invention provides antibody conjugates, including antibody drug conjugates, and methods for preparing antibody conjugates using uncapped antibody. Residual reducing agent can be removed from the antibody preparation prior to preparing antibody drug conjugates.

The invention also provides a method for selectively reducing non-antibody proteins with unpaired cysteine residues. The method includes contacting a reducing agent with protein molecules, each of the protein molecules having at least one capped cysteine residue and at least one inter-chain disulfide bond, and reacting the reducing agent with the protein molecules under conditions sufficient to uncap cysteine residues and form cap byproducts. Cap byproduct is removed during the reduction reaction. The methods result in the formation of an uncapped cysteine protein preparation. The uncapped cysteine protein preparation can contain both capped and uncapped cysteine protein molecules. Substantially all of the inter-chain disulfide bonds present in the protein molecules prior to the reduction reaction are retained in the uncapped cysteine protein preparation. The method can further comprise the step of supplementing the reduction reaction with additional reducing agent while removing cap byproduct. Removing the cap byproduct from the reaction mixture during the reduction reaction can be, for example, via dialysis or diafiltration. In preferred embodiments, the concentration of the cap byproduct is maintained in the reduction reaction mixture below the concentration at which re-capping prevents further activation of cysteine residues. The methods provide an uncapped cysteine protein preparation. Typically, at least about 60% of the capped cysteine residues are uncapped (or, in other words, activated) using said methods. In some aspects, at least about 70%, at least about 75% or at least about 80% of the capped cysteine residues are uncapped using said methods. In some aspects, using said methods, at least 85% of the inter-chain disulfide bonds present in the protein molecules prior to the reduction reaction are retained in the uncapped engineered cysteine antibody preparation. In some aspects, the reducing agent and reducing conditions are selected such that no more than about 20%, no more than about 15%, no more than about 10% or no more than about 5% of the inter-chain disulfide bonds present in the protein molecules are converted during the reduction reaction to a pair of free thiols.

DETAILED DESCRIPTION OF THE INVENTION

I. General

Figure 1:
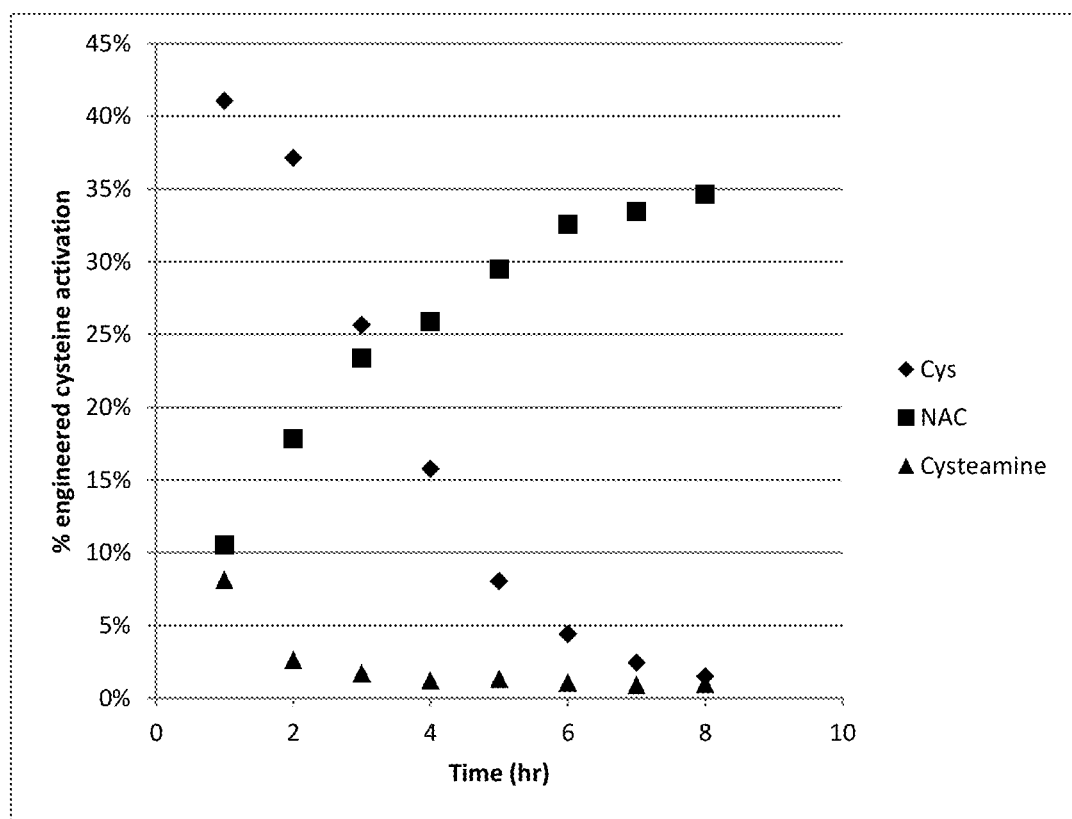
FIG. 1 shows the results of a rPLRP column analysis of samples generated by treating an ecmAb (99 µM in solution) with three different monothiol reducing agents (cysteine, N-acetyl cysteine (NAC), and cysteamine) under identical conditions at low concentration (2 mM). The Y axis represents the % activation of total engineered cysteines available. None of the reducing agents is able to approach 100% activation of the available engineered cysteine residues. There was no evidence of reduction of inter-chain disulfide bonds in these experiments.

The present invention provides, inter alia, methods for selectively removing sulfide caps from engineered cysteine residues in antibodies, including monoclonal antibodies. Although some selective removal is observed after prolonged exposure of antibodies to small molecule thiols at low concentrations, complete cap removal does not occur in a static reaction mixture. Advantageously, nearly complete activation of engineered cysteines can be achieved by utilizing the methods of the invention in which the reducing agent concentration is maintained while reduction byproducts are removed. In embodiments where it is not desired to activate substantially all of the engineered cysteines, the present methods can be used to control the level of activation. Surprisingly, the uncapped antibodies are obtained with interchain disulfide bonds intact, preserving antibody structure and eliminating the need for a reoxidation step prior to conjugation of the antibodies with drug or other functional agents. The methods of the invention provide, inter alia, a significant simplification of current manufacturing practice for preparation of antibody conjugates, including antibody drug conjugates.

II. Definitions

As used herein, the terms "antibody" broadly refers to intact monoclonal antibodies, polyclonal antibodies, monospecific antibodies, multispecific antibodies (e.g., bispecific antibodies), and antibody fragments that exhibit the desired biological activity (i.e., specific binding to a target antigen) and that have at least one native inter-chain disulfide bond. Exemplary fragments include, for example, Fabs, minibodies and the like. An intact antibody is typically composed of four polypeptide chains (two heavy chains and two light chains), each polypeptide having primarily two regions: a variable region and a constant region. The variable region specifically binds to and interacts with a target antigen. The variable region includes complementarity determining regions (CDRs) that recognize and bind to a specific binding site on a particular antigen. The constant region may be recognized by and interact with the immune system (see, e.g., Janeway et al., 2001, Immuno. Biology, 5th Ed., Garland Publishing, New York). The four polypeptide chains are covalently linked to each other via inter-chain disulfide bonds. An antibody can be of any type (e.g., IgG, IgE, IgM, IgD, and IgA), class (e.g., IgG1, IgG2, IgG3, IgG4, IgA1 and IgA2) or subclass. The antibody can be derived from any suitable species. In some embodiments, the antibody is of human or murine origin. A monoclonal antibody can be, for example, human, humanized, or chimeric. Depending on the context, the term "antibody" can refer to a singular antibody molecule or a collection of antibody molecules, such as in an antibody solution.

As used herein, the term "inter-chain disulfide bond" refers to a covalent bond between two cysteine residues on adjacent polypeptide chains in an antibody. The disulfide bond has the formula $R^1$—S—$R^2$, wherein the sulfur atoms are present in the cysteine sidechains and $R^1$ and $R^2$ represent the remainder of the cysteine residues and the polypeptide chains in which they reside. An inter-chain disulfide bond is generally present between a heavy chain and a light chain in an antibody, or between the two heavy chains.

As used herein, the term "engineered cysteine residue" refers to a cysteine residue that is introduced into the peptide sequence of a protein (e.g., antibody). A monoclonal antibody having an engineered cysteine residue can be referred to as an "ecmAb." The engineered cysteine residue is generally not present in the native (i.e., naturally-occurring) peptide sequence of the protein. The engineered cysteine residue can take the place of the amino acid that naturally occurs at a given position in the peptide sequence, and can be introduced into the peptide sequence via recombinant techniques such as site-directed mutagenesis. The engineered cysteine residue can be capped or uncapped.

As used herein, the term "uncapped cysteine residue" refers to a cysteine residue wherein the α-sidechain contains a free thiol moiety having the formula $R^1$—SH. $R^1$ represents the non-thiol portion of the cysteine residue. The uncapped cysteine residue can be an uncapped engineered cysteine residue.

As used herein, the term "capped cysteine residue" refers to a cysteine residue wherein the α-sidechain contains a disulfide moiety having the formula $R^1$—S—S—$R^3$. $R^1$ represents the non-thiol portion of the cysteine residue, and $R^3$ represents the non-thiol portion of a capping moiety having a molecular weight less than or equal to about 500 Da. The cap can be, for example, cysteine, cysteinyl glycine, or glutathione (with $R^3$ representing the non-thiol portion of free cysteine, cysteinyl glycine, or the non-thiol portion of glutathione, respectively) or any other available monothiol. The capped cysteine residue can be a capped engineered cysteine residue.

As used herein, the term "reduction reaction" refers to a reaction wherein a capped cysteine residue (e.g., capped engineered cysteine residue) having the formula $R^1$—S—S—$R^3$ is reduced and forms a thiol moiety having a structure $R^1$—SH. $R^1$ and $R^3$ are defined as in the above descriptions.

As used herein, the term "reducing agent" refers to a compound that can reduce disulfide bonds. Reducing agents include, but are not limited to, thiols such as cysteine, cystamine, and β-mercaptoethanol.

As used herein, the term "oxidizing agent" refers to a compound that causes the conversion of a pair of free thiols to a disulfide bond. Examples of oxidizing agents include, but are not limited to, 5,5'-dithiobis(2-nitrobenzoic acid) (DTNB), dehydroascorbic acid (DHAA), and copper sulfate (CuSO4). "A re-oxidation step" is an affirmative step that is taken to cause the conversion of a pair of free thiols to a disulfide bond. Affirmative steps include introduction of an exogenous oxidizing agent and/or an intentional hold period to allow for autoxidation.

As used herein, "removing" a substance, such as a cap byproduct, from a mixture containing an antibody and the substance refers to removing any portion of the substance, including the entirety of the substance, from the mixture. Removing the substance can also include transferring the antibody from a first mixture containing the substance to a second mixture not containing the substance. Removing a substance from a mixture can include steps such as dialysis, diafiltration, chromatography, and the like.

As used herein, the terms "antibody-drug conjugate" and "ADC" refer to an antibody conjugated to a therapeutic agent, (i.e., a drug) optionally via a linker.

As used herein, the term "drug-linker compound" or "drug-linker" refers to a molecule having a drug moiety and a linker attached thereto, wherein the linker contains a reactive moiety suitable for attachment to an amino acid residue (such as a cysteine residue) in an antibody.

III. Description of the Embodiments

The present invention provides, inter alia, a method for selectively reducing engineered cysteine antibodies thereby forming an uncapped antibody preparation. The method includes contacting a reducing agent with engineered cysteine antibody molecules, each of the antibody molecules having at least one capped engineered cysteine residue and at least one inter-chain disulfide bond and reacting the reducing agent with the antibody molecules under conditions sufficient to uncap engineered cysteine residues and form cap byproducts. During the reduction reaction, the cap byproduct is removed, thereby preventing re-capping of the newly formed thiols. Reducing agent, eliminated along with the cap byproduct, is replaced to drive the reduction reaction forward. The reducing agent and conditions are selected such that the engineered cysteine residues are selectively reduced (i.e., selectively activated). As a result, a separate re-oxidation step is not required in order to reform interchain disulfide bonds following the reduction step. Substantially all of the interchain disulfide bonds present in the antibody molecules having the capped engineered cysteine residues are retained in the uncapped antibody preparation. By use of the term "retain" it is not meant that the interchain disulfide bonds necessarily remain intact during the reduction reaction. Bonds may be broken during the reduction but they reform prior to conversion into a pair of free thiols. Bond reformation is not dependent on a separate re-oxidation step but occurs during the reduction reaction as shown in Scheme 2.

Scheme 1 shows a schematic representation of cysteine residue uncapping according to the methods of the invention, with a monoclonal antibody as the exemplary protein. As shown in reaction (i), reaction of a reducing agent (1) with an antibody having a capped engineered cysteine residue (2) results in an antibody having an uncapped engineered cysteine residue (3) and a cap byproduct (4). Reaction (i) can proceed in both directions, and reaction of the uncapped engineered cysteine residue with the cap byproduct can result in recapping of the engineered cysteine residue. The result of the back reaction is a composition in which only some of the antibodies in the composition have an uncapped engineered cysteine residue. According to the methods of the invention, the reaction mixture is supplemented with additional reducing agent as shown in reaction (ii) and cap byproduct is removed from the reaction mixture. Reducing agent supplementation and cap byproduct removal can drive the reaction forward and prevent the back reaction, promoting the formation of the desired antibody having the uncapped engineered cysteine residue (3).

Scheme 1

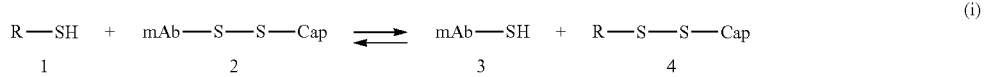

(i)

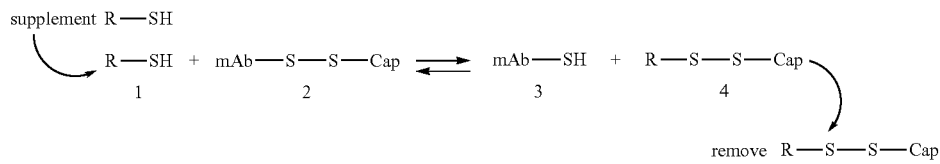

(ii)

Under normal (i.e. "static solution") conditions, the re-capping reaction limits the extent of activation of engineered cysteines. The graph in FIG. 1 shows the results of treating an ecmAb with three different monothiols under identical conditions. The Y axis represents the % activation of total engineered cysteines available. The graph shows that none of the reducing agents is able to approach 100% activation of the available engineered cysteine residues, and this limitation is because the disulfide byproduct (4, Scheme 1) re-caps the generated thiol, as described above.

Reducing Agents

Any suitable reducing agent can be used in the methods of the invention. Examples of reducing agents include, but are not limited to, monothiol reducing agents such as cysteine, N-acetyl cysteine, cysteamine, β-mercaptoethanol, 2-mercaptoethanesulfonic acid sodium salt, and the like. Mild reducing agents such as cysteine and the like are particularly suitable for removing the cap from a capped cysteine residue (e.g., capped engineered cysteine residue) without reducing interchain disulfide bonds. Stronger reducing agents, such as dithiothreitol (DTT), dithioerythritol (DTE), and bis(2-mercaptoethyl)sulfone), can reduce inter-chain disulfide bonds too quickly in many cases. In particular, reducing agents such as TCEP and DTT, for which the mixed disulfide of intermediate 6 of Scheme 2 either does not form, or forms only transiently, are unlikely to selectively uncap capped cysteines. In some embodiments, the reducing agent is selected from cysteine, cysteamine, β-mercaptoethanol, 2-mercaptoethanesulfonic acid sodium salt, and mixtures thereof.

Reaction Conditions

While many monothiols can be used for selective activation, the graph in FIG. 1 shows that different thiols activate engineered cysteines at different rates, and to different maximal levels. Hence, identifying suitable conditions for activation of engineered cysteine residues involves identifying a suitable reducing agent and identifying a suitable concentration of the reducing agent.

Reaction conditions will be determined, in part, by the location of the engineered cysteine residue, the identity of the cap, or residues in a particular antibody. Solvent-exposed engineered cysteine residues, for example, can be uncapped more readily than buried or partially-buried engineered cysteine residues.

Conditions favoring selective activation of unpaired cysteine residues in proteins can be understood based on the reactions in Scheme 2. If a reducing reagent reacts with an engineered cysteine residue—as in reaction (a)—very much faster than with an inter-chain disulfide bond as in reaction (b), then selective activation may be relatively straightforward. This condition occurs only, if ever, when the engineered cysteine is highly exposed to solvent on the antibody surface. Frequently, however, less exposed locations are preferred for engineered cysteine residues in ecmAbs used in antibody conjugates such as ADCs. Reducing agents can react with these less exposed engineered cysteine residues and with disulfide bonds at comparable rates. As such, it is often necessary to find selective activation conditions when reactions (a) and (b) occur at comparable rates.

In cases where reactions (a) and (b) occur at comparable rates—or where reaction (b) is faster than reaction (a)—selective activation of the engineered cysteine requires ensuring that when an inter-chain disulfide is attacked by the reducing agent, the reaction (c) to re-form the disulfide is faster than the second reduction step (d), which results in the undesired cleavage of an inter-chain disulfide. In general, it is not possible to impact the rate of reaction (c), because it is a unimolecular reaction. The thiol and mixed disulfide shown in 6 are part of the same antibody. The rate of reaction (d), however, is dependent on the concentration of reductant, so reaction (d) can be made to be slower than reaction (c) by using a sufficiently low concentration of reducing agent. Of course, reactions (a) and (b) are also dependent on the concentration of reducing agent, so under these conditions activation is also slow. Hence, selective activation of engineered cysteines is generally favored by the maintenance of very mild reduction conditions (low concentration of reducing agent, and relatively mild reducing agent) over a long period of time.

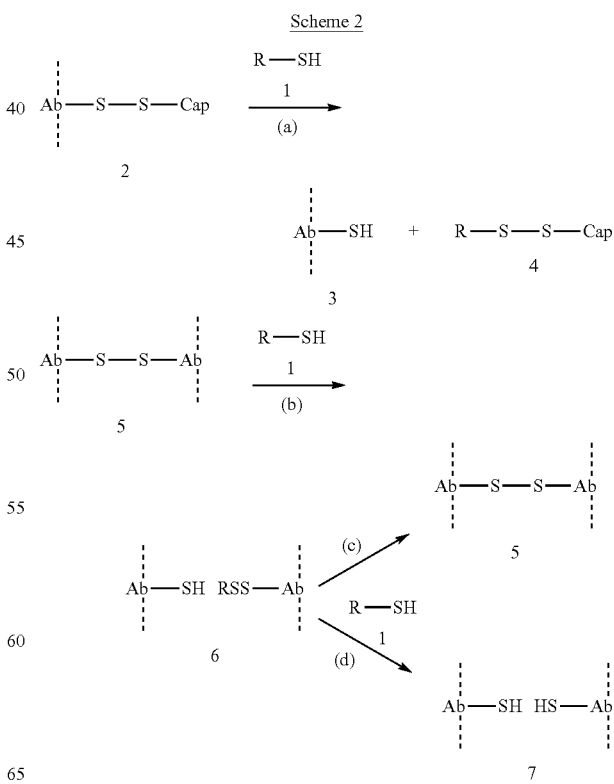

Scheme 2

Reduction reaction mixtures can include any suitable amount of protein. Typically, the concentration of protein (whether antibody or non-antibody protein) in the reduction reaction mixture ranges from about 0.01 mg/mL to about 150 mg/mL, more typically from about 1 mg/ml to about 50 mg/ml. The reduction reaction mixture can contain, for example, about 0.01, 0.05, 0.1, 0.25, 0.5, 1.0, 2.0, 3.0, 4.0, 5.0, 6.0, 7.0, 8.0, 9.0, 10.0, 12.5, 15, 17.5, 20, 22.5, 25, 30, 35, 40, 45, 50, 55, 60, 65, 70, 75, 80, 85, 90, 95, 100, 110, 120, 130, 140, or about 150 mg of protein (whether antibody or non-antibody protein) per mL of reduction reaction mixture. The concentration of protein (whether antibody or non-antibody protein) can be higher or lower, depending on the particular reaction conditions employed. One of skill in the art will be able to convert a mass-based concentration (e.g., mg/mL) to a molar concentration (i.e., moles/L).

Any suitable amount of reducing agent can be used in the methods of invention. In general, the concentration of the reducing agent in the reduction reaction mixture is high enough that the reaction proceeds, but low enough that inter-chain disulfide reduction is negligibly slow. The reduction reaction mixture is typically formed using an initial amount of the reducing agent at an initial concentration. This initial concentration is substantially maintained by supplementing the reduction reaction mixture with additional amounts of the reducing agent in a continuous or step-wise fashion through the duration of the reduction reaction. In certain embodiments, the reduction reaction mixture is supplemented with additional amounts of the reducing agent in a continuous fashion throughout the reduction reaction. The optimal concentration of reducing agent can be experimentally determined using the teachings described herein, and will be different for different thiols because of their different reduction strengths. It was determined that an optimal concentration of cysteine using the conditions described in the examples, is about 0.5 mM to about 1.5 mM. Depending on the strength of the reducing agent and the concentration of ecmAb, that concentration may be increased or decreased. In some embodiments, the concentration of reducing agent will be maintained at a concentration greater than the concentration of total antibody. The optimal concentration ratio of reducing agent to total antibody will also be dependent on the strength of the reducing agent. The concentration of reducing agent in the reduction reaction mixture will, in some aspects, be about 5 times to about 25 times, 5 times to about 20 times, 5 times to about 15 times, or 5 times to about 10 times higher than the concentration of total antibody in the reduction reaction mixture. For example, in some embodiments, the concentration ratio of reducing agent to total antibody in the reduction reaction mixture will be about 5:1, 6:1, 7:1, 8:1, 9:1, 10:1, 11:1, 12:1, 13:1, 14:1, 15:1, 16:1, 17:1, 18:1, 19:1, or 20:1. In some embodiments, including some embodiments when the reducing agent is cysteine, the concentration ratio of reducing agent to total antibody in the reduction reaction mixture will be from about 5:1 to about 12:1, from about 7:1 to about 10:1, preferably about 8:1. In some such aspects, the engineered cysteine residue will be at position 239 of the heavy chain (numbering according to the EU index). Other concentration ratios can be used in the methods of the invention, depending on factors such as the particular reducing agent being used or the location of the engineered cysteine residue in the antibody.

The reduction reaction to uncap the cysteine residues (engineered or native cysteine residues) is conducted such that it minimizes reduction of the interchain disulfide bonds and the subsequent generation of free thiols. Substantially all of the inter-chain disulfide bonds present in the protein having the capped cysteine residues are retained in the uncapped protein preparation formed using the present methods. In general, at least about 80% of the inter-chain disulfide bonds are retained in the uncapped protein preparation. In certain embodiments, at least about 85% of the inter-chain disulfide bonds are retained in the uncapped protein preparation. In certain embodiments, at least about 90% or about 95% of the inter-chain disulfide bonds are retained in the uncapped protein preparation. In certain embodiments, all of the inter-chain disulfide bonds are retained in the uncapped protein preparation. Or, in other words, in exemplary embodiments, no more than about 20%, no more than about 15%, no more than about 10%, or no more than about 5% of the inter-chain disulfide bonds are converted during the reduction reaction to a pair of free thiols. As it applies to antibodies, substantially all of the inter-chain disulfide bonds present in the antibody molecules having the capped engineered cysteine residues (e.g., antibody molecules prior to the reduction reaction) are retained in the uncapped antibody preparation formed using the present methods. In general, at least about 80% of the inter-chain disulfide bonds are retained in the uncapped antibody preparation. In certain embodiments, at least about 85% of the inter-chain disulfide bonds are retained in the uncapped antibody preparation. In certain embodiments, at least about 90% or about 95% of the inter-chain disulfide bonds are retained in the uncapped antibody preparation. In certain embodiments, all of the inter-chain disulfide bonds are retained in the uncapped antibody preparation. Or, in other words, in exemplary embodiments, no more than about 20%, no more than about 15%, no more than about 10%, or no more than about 5% of the inter-chain disulfide bonds are converted during the reduction reaction to a pair of free thiols.

While the concentration of the reducing agent is maintained in the reduction reaction mixture, reduction byproducts are removed from the reduction reaction mixture. Reducing agent addition and byproduct removal can be conducted in a continuous or step-wise fashion. In certain embodiments, reducing agent addition and byproduct removal are conducted in a continuous fashion. Reducing agent can be added and byproducts can be removed by techniques including, but not limited to, tangential flow filtration (e.g., diafiltration) size exclusion chromatography, solid phase immobilization, and dialysis. In a diafiltration process, an aqueous reducing agent solution is typically added to the reduction reaction mixture at a given flow rate while a portion of the mixture is removed at about the same flow rate. A semi-permeable membrane can be used to retain the protein (e.g., antibody) in the reduction reaction mixture. Alternatively, the protein (e.g., antibody) can be immobilized on a solid support (such as Protein A agarose beads) and the aqueous reducing agent solution can be passed across the immobilized protein (e.g., antibody). A reactive resin that reacts with the cap byproduct can also be used. For example, cap byproduct can be sequestered using resins that have reactive moieties such as disulfides on the interior of pores small enough to exclude the protein (e.g., antibody).

Accordingly, some embodiments of the invention provide methods as described above wherein removing the cap byproduct from the reduction reaction mixture comprises dialyzing or diafiltering the reduction reaction mixture during the reduction reaction. In some embodiments, removing the cap byproduct from the reduction reaction mixture comprises diafiltering the reduction reaction mixture during the reduction reaction.

Often, the methods of the invention are conducted so as to maximize the uncapping of cysteine residues. Any one protein molecule, however, can have capped cysteine residues as well as uncapped residues. Often, an uncapped antibody preparation will contain two or more of: an antibody molecule having at least two uncapped engineered cysteine residues and no capped engineered cysteine residues; an antibody molecule having at least two capped engineered cysteine residues and no uncapped engineered cysteine residues; and an antibody molecule having at least one capped engineered cysteine residue and at least one uncapped engineered cysteine residue. Advantageously, the methods of the invention provide high levels of selectively-uncapped engineered cysteine residues. For example, the methods can be conducted such that at least 40% of the engineered cysteine residues are uncapped. In some aspects, the methods can be conducted such that at least about 40%, at least about 45%, at least about 50%, at least about 55%, at least about 60%, at least about 65%, at least about 70%, at least about 75%, at least about 80%, at least about 85%, or at least about 90% of the engineered cysteine residues are uncapped. In certain embodiments, at least 60% of the engineered cysteine residues are uncapped. Higher or lower levels of uncapping can also occur, depending in part on the particular antibody as well as the location of the engineered cysteine residues within the antibody. Although, the methods of the invention are generally conducted so as to maximize the uncapping of cysteine residues, there may be instances when maximizing uncapping of cysteine residues is not desired, for example, with an antibody having two engineered cysteine residues when it is desired to only conjugate one of the cysteine residues to a functional agent. In some such embodiments, the present methods can be used to tightly control activation of engineered cysteine residues. An advantageous aspect of the method of the invention is that intermediate levels of uncapping are readily attainable simply by stopping the activation at the desired level and conjugating. Such intermediate conjugates are difficult to obtain when using the method of complete reduction followed by re-oxidation.

Reaction mixtures can contain additional reagents or components. As non-limiting examples, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), co-solvents (e.g., dimethylsulfoxide, dimethylformamide, ethanol, methanol, isopropanol, glycerol, tetrahydrofuran, acetone, acetonitrile, and acetic acid), salts (e.g., NaCl, KCl, $CaCl_2$), and salts of $Mn^{2+}$ and $Mg^{2+}$), denaturants (e.g., urea and guandinium hydrochloride), detergents (e.g., sodium dodecylsulfate and Triton-X 100), and chelators (e.g., ethylene glycol-bis(2-aminoethylether)-N,N,N',N'-tetraacetic acid (EGTA), 2-({2-[Bis(carboxymethyl)amino]ethyl} (carboxymethyl)amino)acetic acid (EDTA), and 1,2-bis(o-aminophenoxy)ethane-N,N,N',N'-tetraacetic acid (BAPTA)). Buffers, co-solvents, salts, denaturants, detergents, and chelators can be used at any suitable concentration, which can be readily determined by one of skill in the art. In general, buffers, co-solvents, salts, denaturants, detergents, and chelators if present, are included in reaction mixtures at concentrations ranging from about 1 µM to about 1 M. For example, a buffer, a co-solvent, a salt, a denaturant, a detergent, or a chelator can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M. Cosolvents, in particular, can be included in the reaction mixtures in amounts ranging from, for example, about 1% v/v to about 75% v/v, or higher. A cosolvent can be included in the reaction mixture, for example, in an amount of about 5, 10, 20, 30, 40, or 50% v/v.

Reactions are conducted under conditions sufficient to form uncapped cysteine residues. The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 6.5 to about 10. In certain instances, the pH is from about 7.0 to about 8.5. The reactions can be conducted for any suitable length of time. The length of time selected will be dependent on the strength of the reducing agent. Because mild reduction conditions (low concentration of reducing agent, and relatively mild reducing agent) are used in the present methods, the reduction reaction will extend longer than typically expected for reduction of inter-chain disulfide bonds. In some preferred aspects, the reduction reaction will proceed until at least about 60%, at least about 70% or at least about 80% or at least about 85% of the capped engineered cysteine residues are uncapped. In some aspects, the reduction reaction will be incubated under suitable conditions for at least one hour, at least two hours, at least three hours, at least four hours, at least five hours, or at least about 6 hours. Reactions can be conducted under an inert atmosphere, such as a nitrogen atmosphere or argon atmosphere. Other reaction conditions can be employed in the methods of the invention, depending on the identity of a particular antibody, or reducing agent.

In some embodiments, the pH of the reaction mixture ranges from about 6.5 to about 8.5. In some embodiments, the methods of the invention include maintaining the reaction mixture at a temperature ranging from about 4° C. to about 37° C. In some embodiments, the reaction mixture is maintained at a desired temperature for a period of time ranging from about 1 hour to about 8 hours.

A number of known purification techniques can be employed at various points during the methods of the invention. Such techniques can be used to remove excess reducing agents, to exchange buffers or other components into and out of reaction mixtures, and to concentrate or dilute antibody compositions as necessary. Purification techniques useful in the methods of the invention include, but are not limited to, tangential flow filtration (TFF), gel filtration, immunoprecipitation, affinity chromatography, and the like. Preferably, purification time is minimized to prevent unwanted oxidation or re-capping of uncapped engineered cysteine residues.

Antibody Conjugates

Uncapped engineered cysteine residues on an antibody serve as useful handles for installation of a variety of functional groups, including imaging agents (such as chromophores and fluorophores), diagnostic agents (such as MRI contrast reagents and radioisotopes), stability agents (such as polyetheylene glycol polymers) and therapeutic agents. Antibodies having uncapped cysteine residues can be conjugated to functional agents to form antibody-functional agent-conjugates. The functional agent (e.g., drug, detection agent, stability agent) is conjugated (covalent attachment) to the antibody at the site of an engineered cysteine residue. A functional agent can be attached indirectly via a linker or directly via a thiol-reactive group on the functional agent.

Antibodies having uncapped cysteine residues can be conjugated to drugs to form antibody drug conjugates (ADCs). Typically, the ADC contains a linker between the drug and the antibody. The linker can be a cleavable or a non-cleavable linker. A cleavable linker is typically susceptible to cleavage under intracellular conditions such that cleavage of the linker releases the drug from the antibody at the target site. Suitable cleavable linkers include, for example, enzyme cleavable linkers including peptidyl containing linkers cleavable by an intracellular protease, such as lysosomal protease or an endosomal protease or sugar linkers for example, glucuronide containing linkers cleavable by a glucuronidase. Peptidyl linkers can include, for example, a dipeptide, such as valine-citrulline (val-cit) phenylalanine-lysine (phe-lys) or valine-alanine (val-ala). Other suitable cleavable linkers include, for example, pH-sensitive linkers (e.g., linkers hydrolyzable at a pH of less than 5.5, such as a hydrazone linker) and linkers cleavable under reducing conditions (e.g., disulfide linkers). Non-cleavable linkers typically release drugs by proteolytic degradation of the antibody.

Prior to attachment to the antibody, the linker will have a group reactive with the uncapped engineered cysteine residues and attachment will be via the reactive group. Thiol-specific reactive groups are preferred and include, for example, maleimides; haloacetamides (e.g., iodo, bromo or chloro); haloesters (e.g., iodo, bromo or chloro); halomethyl ketones (e.g., iodo, bromo or chloro); benzylic halides (e.g., iodide, bromide or chloride); vinyl sulfones; (pyridyl)disulfides; disulfide dioxide derivatives; mercury derivatives such as 3,6-bis-(mercurimethyl)dioxane with counter ions of acetate, chloride or nitrate; and polymethylene bismethane thiosulfonates. The linker can include, for example, a maleimide that attaches to the antibody via a thio-succinimide linkage.

The drug can be any cytotoxic, cytostatic or immunosuppressive drug. In embodiments wherein a linker links the antibody and the drug, the drug has a functional group that can form a bond with the linker. For example, the drug can have an amine, a carboxylic acid, a thiol, a hydroxyl group, or a ketone that can form a bond with the linker. In aspects wherein the drug is directly attached to the linker, the drug will, prior to attachment to the antibody, have a group reactive with the uncapped engineered cysteines.

Useful classes of drugs include, for example, antitubulin agents, DNA minor groove binders, DNA replication inhibitors, alkylating agents, antibiotics, antifolates, antimetabolites, chemotherapy sensitizers, topoisomerase inhibitors, vinca alkaloids, or the like. Particularly examples of useful classes of cytotoxic agents include, for example, DNA minor groove binders, DNA alkylating agents, and tubulin inhibitors. Exemplary cytotoxic agents include, for example, auristatins, camptothecins, duocarmycins, etoposides, maytansines and maytansinoids (e.g., DM1 and DM4), taxanes, benzodiazepines or benzodiazepine containing drugs (e.g., pyrrolo[1,4]-benzodiazepines (PBDs), indolinobenzodiazepines, and oxazolidinobenzodiazepines) and vinca alkaloids. Select benzodiazepine containing drugs are described in WO 2010/091150, WO 2012/112708, WO 2007/085930, and WO 2011/023883.

In some typical embodiments, suitable cytotoxic agents include, for example, DNA minor groove binders (e.g., enediynes and lexitropsins, a CBI compound; see also U.S. Pat. No. 6,130,237), duocarmycins (see U.S. Publication No. 20060024317), taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

The drug can be an anti-tubulin agent. Examples of anti-tubulin agents include, but are not limited to, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, auristatins, and eleutherobin.

The drug can be a maytansine or a maytansinoid, another group of anti-tubulin agents. (ImmunoGen, Inc.; see also Chari et al., 1992, Cancer Res. 52:127-131 and U.S. Pat. No. 8,163,888).

The drug can be an auristatin. Auristatins include, but are not limited to, AE, AFP, AEB, AEVB, MMAF, and MMAE. The synthesis and structure of auristatins are described in U.S. Patent Application Publication Nos. 2003-0083263 and 2009-0111756; International Patent Publication No. WO 04/010957; International Patent Publication No. WO 02/088172; U.S. Pat. Nos. 6,884,869; 7,659,241; 7,498,298; 8,343,928; and 8,609,105; each of which is incorporated by reference in its entirety and for all purposes.

In some embodiments, the drug moiety is selected from the group consisting of an anti-tubulin agent, a DNA binding agent, and a DNA alkylating agent. In some embodiments, the drug is selected from the group consisting of an auristatin, a pyrrolobenzodiazepine, a duocarmycin, a maytansinoid, a taxane, a calicheamicin, and an anthracycline.

A drug-linker can be used to form an ADC in a single step. In other embodiments, a bifunctional linker compound can be used to form an ADC in a two-step or multi-step process. In one example, the uncapped engineered cysteine residue is reacted with the reactive moiety of a linker in a first step, and a functional group on the linker is reacted with a drug to form the ADC in a subsequent step.

Generally, a functional group on the linker is selected for specific reaction with a suitable reactive group in the drug moiety. As a non-limiting example, an azide-based moiety can be used for specific reaction with a reactive alkyne group in the drug moiety. The drug is covalently bound to the linker via 1,3-dipolar cycloaddition of the azide and alkyne. Other useful functional groups include, for example, ketones and aldehydes (suitable for reaction with hydrazides and alkoxyamines); phosphines (suitable for reaction with azides); isocyanates and isothiocyanates (suitable for reaction with amines and alcohols); and activated esters such as N-hydroxysuccinimidyl esters (suitable for reaction with amines and alcohols). These and other linking strategies, as described, for example, in *Bioconjugate Techniques*, $2^{nd}$ Ed. (Elsevier), are well known to those of skill in the art. One of skill in the art will appreciate that when a complementary pair of reactive functional groups is chosen for selective reaction of the drug moiety to the linker, each member of the pair can be employed on either the linker or the drug.

Accordingly, some embodiments of the invention provide methods for preparing an uncapped antibody preparation as described above, further including combining uncapped antibody (e.g., combining the uncapped antibody preparation) with a drug-linker compound under conditions sufficient to form an antibody-drug conjugate (ADC).

In some embodiments, the methods include combining uncapped antibody with a bifunctional linker compound, under conditions sufficient to form an antibody-linker conjugate. In such embodiments, the methods of the invention can further include combining the antibody-linker conjugate with a drug moiety under conditions sufficient to covalently link the drug moiety to the antibody via the linker.

In some embodiments, the ADC is of the following formula:

wherein
  Ab is an antibody,
  LU is a linker,
  D is a drug;
  and the subscript p is a value from 1 to 8.

In the formula above, the linker, LU, is conjugated to the antibody via the uncapped engineered cysteines. The value of the subscript p is dependent on the number of uncapped engineered cysteines available for conjugation. For example, for an antibody having two uncapped engineered cysteines, (e.g., one site on each heavy chain or one site on each light chain), the value of p can be two. Similarly, for an antibody having four uncapped engineered cysteines (e.g., two sites on each heavy chain, or two sites on each light chain, or one site on each heavy chain and one site on each light chain), the value of p can be four. In some preferred embodiments, p is a value from 1 to 4.

Drug Loading

The average number of drug-linker molecules per antibody (or average drug load) is an important characteristic of an ADC composition, as it is a primary determinant of the amount of drug that can be delivered to a target cell. The average drug load includes drugs conjugated to engineered cysteine residues, as well as drugs conjugated to sites other than the intended engineered cysteine residues and the amount of unconjugated antibodies in the composition. When an average drug loading of about two drugs per antibody is targeted, antibodies having two engineered cysteine residues (e.g., one site on each heavy chain or one site on each light chain) can be used to prepare the ADC composition. When an average drug loading of about four drugs per antibody is targeted, antibodies having four engineered cysteine residues (e.g., two sites on each heavy chain, or two sites on each light chain, or one site on the heavy chain and one site on the light chain) can be used to prepare the ADC composition. One of skill in the art will appreciate that other levels of drug loading can be therapeutically useful depending on the particular antibody or the particular drug (including, for example, drug loading levels less than 2 as well as drug loading levels greater than 4). Sites for drug conjugation can be introduced in an antibody by placing engineered cysteines at more than one site or more than two sites in the heavy chain, or by placing an engineered cysteine in the light chain, or both. Importantly, the level of engineered cysteine residue uncapping described above allows for preparation of ADC compositions with useful drug loading.

Typically, ADC compositions prepared with antibodies having two engineered cysteine residues have an average drug-loading of from about 1.5 to 2.5 drugs per antibody. The average number of drug moieties per antibody can be, for example, about 1.5, 1.6, 1.7, 1.8, 1.9, 2.0, 2.1, 2.2, 2.3, 2.4, or 2.5. In some embodiments, the average drug-loading for ADC compositions prepared with antibodies having two engineered cysteine residues is from about 1.5 to about 2.2 drug moieties per antibody, or from about 1.8 to about 2 drug moieties per antibody. Typically, ADC compositions prepared with antibodies having four engineered cysteine residues have an average drug-loading of from about 3.4 to 4.5 drug moieties per antibody. The average number of drug moieties per antibody can be, for example, about 3.3, 3.4, 3.5, 3.6, 3.7, 3.8, 3.9, or 4.0. In some embodiments, the average drug-loading for ADC compositions prepared with antibodies having four engineered cysteine residues is from about 3.6 to about 4.2 drug moieties per antibody, or from about 3.8 to about 4 drug moieties per antibody.

The methods of the invention are typically conducted so as to selectively modify uncapped engineered cysteine residues, but varying degrees of non-engineered (i.e., native) cysteine residue modification are commonly observed. Reaction conditions can be controlled to limit the modification of non-engineered cysteine residues as necessary. In certain instances, the methods can be conducted to eliminate or minimize modification of non-engineered cysteine residues. For example, the methods can be conducted such that no more than about 20%, no more than about 15%, no more than about 10%, or no more than about 5% of the antibody molecules in the ADC composition have a drug moiety covalently linked to a non-engineered cysteine residue. The methods can also be used to prepare ADC compositions wherein the number of antibody molecules with modified non-engineered cysteine residues amount to no more than about 5%, 10%, 15%, 20%, 25%, or 30% of the total antibody molecules.

Various analytical methods can be used to determine the yields and isomeric mixtures of the conjugates. Following conjugation of the drug to the antibody, the conjugated drug-antibody species can be separated. In some embodiments, the conjugated antibody species can be separated based on the characteristics of the antibody, the drug and/or the conjugate. Other techniques useful for analysis of ADC compositions include, but are not limited to, reversed-phase chromatography, capillary electrophoresis, and mass spectrometry. ADC compositions can be analyzed, for example, by LC/MS coupled with proteolytic digestion to determine the location of a drug moiety in an ADC.

Antibodies

A number of suitable antibodies can be used in the methods of the invention. Antibodies used in the methods of the invention are useful for a number of applications, including in vitro or in vivo diagnosis, in vivo imaging, and therapy for diseases and conditions associated with distinctive antigens. Five human antibody classes (IgG, IgA, IgM, IgD and IgE), as well as various subclasses (e.g., IgG1, IgG2, IgG3, IgG4, IgA1 and IgA2) within these classes, are recognized on the basis of structural differences, such as the number of immunoglobulin units in a single antibody molecule, the disulfide bridge structure of the individual units, and differences in chain length and sequence. The class and subclass of an antibody is referred to as the antibody's isotype.

The antibody can be an intact antibody or an antigen-binding antibody fragment, provided that the antibody fragment contains at least one inter-chain disulfide bond.

Typically, the antibodies are human, rodent (e.g., mouse and rat), donkey, sheep, rabbit, goat, guinea pig, camelid, horse, or chicken. The antibody can be, for example, a murine, a chimeric, humanized, or fully human antibody produced by techniques well-known to one of skill in the art. Recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as those having a variable region derived from a murine monoclonal and human immunoglobulin constant regions. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art. As used herein, "human" antibodies include antibodies having the amino acid sequence of a human immunoglobulin and include antibodies isolated from human immunoglobulin libraries, from human B cells, or from animals transgenic for one or more human immunoglobulin, as described for example in U.S. Pat. Nos. 5,939,598 and 6,111,166.

The antibodies may be monospecific, bispecific, trispecific, or of greater multispecificity.

In certain instances, the constant domains have effector function. The term antibody effector function, as used herein refers to a function contributed by an Fc domain(s) of an Ig. Such function can be effected by, for example, binding of an Fc effector domain(s) to an Fc receptor on an immune cell with phagocytic or lytic activity or by binding of an Fc effector domain(s) to components of the complement system. The effector function can be, for example, "antibody-dependent cellular cytotoxicity" or ADCC, "antibody-dependent cellular phagocytosis" or ADCP, "complement-dependent cytotoxicity" or CDC. In certain instances, the constant domain lack one or more effector functions. Conjugation of a drug-linker compound to an engineered cysteine residue located in an effector function binding domain can modulate the effector function.

The antibodies may be directed against any antigen of interest, such as of medical and/or therapeutic interest. For example, the antigen can be one associated with pathogens (such as but not limited to viruses, bacteria, fungi, and protozoa), parasites, tumor cells, or particular medical conditions. In the case of a tumor-associated antigen (TAA), the cancer may be of the immune system, lung, colon, rectum, breast, ovary, prostate gland, head, neck, bone, or any other anatomical location. Antigens of interest include, but are not limited to, CD30, CD40, Lewis Y, CD70, CD2, CD20, CD22, CD33, CD38, CD40, CD52, HER2, EGFR, VEGF, CEA, HLA-DR, HLA-Dr10, CA125, CA15-3, CA19-9, L6, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti-transferrin receptor, p97, MUC1-KLH, gp100, MART 1, IL-2 receptor, human chorionic gonadotropin, mucin, P21, MPG, and Neu oncogene product.

Some specific useful antibodies include, but are not limited to, antibodies against the CD33 antigen (e.g., a humanized 2H12 antibody as described in International Application Number WO 2013/173496), antibodies against the CD70 antigen, (e.g., a humanized 1F6 antibody as described in International Application Number WO2006/113909), antibodies against the CD30 antigen (e.g., a humanized AC10 antibody as described in International Application Number WO2008/025020), antibodies against the CD19 antigen (e.g., a humanized BU12 antibody as described in International Application Number WO 2009/052431), antibodies against LIV-1, NTBA, or alpha V Beta 6. Many other internalizing antibodies that bind to tumor specific antigens can be used, and have been reviewed (see, e.g., Franke et al. (2000), Cancer Biother Radiopharm. 15:459-76; Murray (2000), Semin Oncol. 27:64-70; Breitling et al., Recombinant Antibodies, John Wiley, and Sons, New York, 1998). The disclosures of these references and International Applications are incorporated by reference herein and for all purposes.

In some embodiments, the invention provides methods for preparing an antibody having an uncapped engineered cysteine residue as described above, wherein the antibody comprises at least three inter-chain disulfide bonds. In some embodiments, the antibody comprises at least four inter-chain disulfide bonds. In some embodiments, the antibody comprises 1, 2, 3, 4, or 5 inter-chain disulfide bonds. In some embodiments, the engineered cysteine residue is present in the heavy constant region or the light constant region of the antibody.

Engineered Cysteine Sites

The site of the engineered cysteine can have an impact on the properties of the ADC. For instance, engineered cysteines entirely buried in the structure of the protein can be difficult to conjugate because of poor access to the solvent, while engineered cysteines on the exterior surface of the antibody may result in ADCs that have impaired stability because of prolonged exposure to materials in plasma. Also, ADCs prepared from ecmAbs with highly surface exposed engineered cysteines may be sensitive to the hydrophobicity of the drug, while engineered cysteines in more protected locations may be less sensitive to the properties of the drug, because access to other materials in solution is restricted. The location of an engineered cysteine residue can also be used to modulate effector function as desired for a particular ADC. For example, conjugation of a drug-linker to an engineered cysteine residue in an effector function binding domain can be used to block binding to effector function-mediating receptors.

In some embodiments, the engineered cysteine is located in the heavy chain constant region, the heavy chain variable region, the light chain variable region, the light chain constant region, or combinations thereof. Preferred engineered cysteine residues are residues that are located at sites that are conjugatable and result in stable linkages. By conjugatable it is meant that the engineered cysteine residue is capable of being conjugated to a functional agent (e.g., imaging agents, diagnostic agents, stability agents or therapeutic agents) without first denaturing the antibody. Methods for selecting a site for introducing a cysteine residue that can be subsequently conjugated to a functional agent are known in the art (e.g., See, for example, Junutula et al., 2008, Nature Biotechnology, 26(8), 925-932)

In some aspects, the engineered cysteine residue is one that has a fractional solvent accessibility of 10% or above, 20% or above, 30% or above, 40% or above, or 50% or above. In some aspects, the cysteine residue is one that has a fractional solvent accessibility of from about 10% to about 95%, from about 10% to about 85%, from about 10% to about 75%, from about 10% to about 60%, from about 20% to about 95%, from about 20% to about 85%, from about 20% to about 75%, from about 20% to about 60%, or from about 40% to about 95%, from about 40% to about 85%, from about 40% to about 75%, from about 40% to about 60%. Methods for determining the fractional solvent accessibility of a residue at a particular site are known in the art and can be determined, for example, using the online server getarea that uses the methodology described in Fraczkiewicz and Braun, 1998, J. Comp. Chem., 19, 319-333 (see http://curie.utmb.edu/getarea.html). Exemplary residues include those at sites 15, 114, 121, 127, 168, 205, on the light chain (numbering according to Kabat) or sites 112, 114, or 116 on the heavy chain (numbering according to Kabat numbering). Exemplary residues includes those in the Fc region of an IgG1 antibody such as those at sites 239, 326, 327, or 269 in the Fc region (numbering according to the EU index). The fraction solvent accessibility of residues at site 239, 326, and 327 is about 50%, about 94%, and about 23%, respectively.

One of skill in the art will recognize that the conditions required for selective activation of the engineered cysteine will be dependent on the site of the engineered cysteine in the antibody. The chemical formulas in Scheme 2 provide a framework for selecting reduction conditions that enable selective activation of engineered cysteines, wherever they occur in the protein sequence. In some embodiments, an antibody has from 1 to 8 or from 2 to 8 or from 2 to 4 engineered cysteine residues.

Non-Antibody Proteins

It will be appreciated by those skilled in the art that although the process described herein is exemplified with respect to antibodies, it may be successfully employed for any protein with unpaired cysteines (cysteines that do not generally form inter-chain or intra-chain bonds within the protein), engineered or native, that are capped with thiols during expression or production. Proteins for which this process is particularly helpful are proteins, that, in addition to comprising unpaired cysteines, contain native cysteines that form inter-chain disulfide bonds, particularly bonds that can be cleaved without immediately resulting in unfolding of the protein. When referring to a non-antibody protein, the term inter-chain disulfide bond refers to a covalent bond between two cysteine residues on adjacent polypeptide chains. Candidate non-antibody proteins include those which contain solvent exposed disulfide bonds whose stability in native folded conformation is comparable to those of the capped thiols. An engineered cysteine protein, as used herein, is one in which selected amino acids in the protein have been mutated to cysteine. Exemplary proteins also include Fc-fusion proteins, e.g., protein containing a Fc region of an antibody covalently linked to a protein that provides specificity for a desired target.

IV. Examples

Example 1: An Exemplary Method for Performing Selective Reduction

A reaction vessel is connected to a tangential flow filtration (TFF) apparatus, and an ultrafiltration membrane is installed (e.g., 88 cm$^2$, Millipore Pelicon 3, regenerated cellulose). (Many different membrane types with appropriate sizes can be used in this process The efflux rate and the sieving factor required for the addition rate calculation for the reducing agent should be determined at the permeate flux and with the membrane type and surface area that will be used in the process). The membrane is flushed and equilibrated according to the manufacturer's instructions. A diafiltration buffer reservoir is set up containing buffer (e.g., 50 mM Tris/5 mM EDTA, pH 8.0). It is connected via tubing to the reaction vessel, and flow through the tubing is controlled by a peristaltic pump (e.g., diafiltration buffer pump). A mAb containing capped engineered cysteines is placed in the reaction vessel. The reaction is performed at room temperature with the reaction mixture continuously pumped past the ultrafiltration membrane, with the retentate line constricted to maintain a trans-membrane pressure of ~20 psi.

A reservoir containing a solution of the reducing agent is connected via tubing to the diafiltration buffer line, or some other location in the flow path or reaction vessel. A flow rate is calculated at which the stock solution containing the reducing agent should be added to the reaction mixture to maintain the initial (desired) concentration of reducing agent in the reaction mixture. (The optimal concentration of reducing agent in the reaction mixture is experimentally determined using the teachings described herein, and will be different for different thiols because of their different reduction strengths as demonstrated in FIG. 1.) The concentration of the reducing agent should remain largely constant over the entire reaction time. Diafiltration buffer is also pumped into the reaction vessel at a rate that is controlled so that the total reaction volume remains constant (as in constant-volume-diafiltration), i.e. the rate of introduction of reducing agent and diafiltration buffer into the reactor matches the rate of volume loss through the permeate.

Example 2. Uncapping Engineered Cysteine Residues Using Cysteine, N-Acetyl Cysteine and Cysteamine as Reducing Agents without Removal of Cap Byproduct A S239C engineered cysteine antibody (IgG1 antibody with an engineered cysteine residue at site 239, numbering according to the EU index), 20 mg (135 nmol at 15 mg/mL) was treated with 33 µL 100 mM (3.3 µmol) cysteine, N-acetyl cysteine, or cysteamine for 8 hours at pH 8.0 and room temperature. Samples were removed at 1 hour intervals, purified, conjugated with excess SGD-1269, and stored frozen. Purification and conjugation stopped the reduction reaction, preserving thiols that had been generated by the reduction procedure. The conjugated samples were analyzed by reversed phase HPLC under denaturing conditions ("rPLRP"), from which the extent of engineered cysteine uncapping could be deduced (conversion of H0 to H1). The extent of inter-chain disulfide cleavage could also be determined from the amount of heavy chain with >1 mcMMAF conjugated (mcMMAF is the maleimido caproic acid linker attached to the drug monomethylauristatin F). No heavy chain was observed with >2 mcMMAF molecules conjugated. Results from the static solution reduction experiments are provided in FIG. 1. The results show that each of the three thiols can react with the ecmAb to uncap the engineered cysteine, but that the three behave quite differently. NAC behaves in a manner that is most directly described by the first reaction in Scheme 1: The reaction proceeds until a sufficient concentration of disulfide 4 has accumulated, then stops because the forward and reverse reactions are occurring at the same rate. Cysteine behaves as a more powerful reductant than NAC, but instead of stopping at partially activated ecmAb, the reaction reverses, regenerating the ecmAb. This reversal indicates that, with cysteine, an additional reaction is involved, namely autoxidation of the reducing agent.

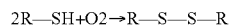
(iii)

Thus, cystine, produced by autoxidation of cysteine, also re-caps activated engineered cysteines, reversing the initial reduction. Examination of FIG. 1 shows that this same phenomenon, initial reduction followed by re-capping, also occurs with cysteamine, but that cysteamine is a weaker reducing agent, so that the initial extent of reduction is not as high as with cysteine or N-acetylcysteine.

Example 3. Selective Activation of Engineered Cysteine Residues in ecmAbs

A reaction vessel was connected to a tangential flow filtration (TFF) apparatus, and ultrafiltration membranes were installed (88 cm², Millipore Pelicon 3, regenerated cellulose). The membrane was flushed and equilibrated according to the manufacturer's instructions. A diafiltration buffer reservoir was set up containing 50 mM Tris/5 mM EDTA, pH 8.0. It was connected via tubing to the reaction vessel, and flow through the tubing was controlled by a peristaltic pump (diafiltration buffer pump). The engineered cysteine mAb containing capped engineered cysteines (h2H12 S239C ecMab, h1F6 239 ecMab, h2H12 K326C ecMab or h2H12 A327C ecMab, numbering according to EU index) was placed in the reaction vessel at a concentration of approximately 15 mg/mL and the pH was adjusted to 8.0. The reaction was performed at room temperature with the reaction mixture continuously pumped past the ultrafiltration membrane, with the retentate line constricted to maintain a trans-membrane pressure of ~20 psi.

A reservoir containing cysteine solution was connected via tubing to the diafiltration buffer line. A flow rate was calculated at which the cysteine stock solution should be added to the reaction mixture to maintain the initial (desired) concentration of cysteine in the reaction mixture. The concentration of the cysteine stock fed into the reaction mixture and the rate of addition were calculated as described below so that the concentration of cysteine remained largely constant over the entire reaction time. In the examples illustrated in FIGS. 2-5, the reaction concentration of cysteine was in the range of 0.5-0.9 mM (as described in the figure descriptions); the stock concentration of cysteine was either 100 mM, 10 mM, or 5 mM, and the flow rate of cysteine pumped into the reactor was adjusted to maintain the experimental cysteine concentration according to the formula below. The sieving factor for the cysteine was measured at 0.8-0.9. Cysteine concentration in the reaction mixture was determined periodically through the experiment using the DTNB assay to ensure that the cysteine level remained at the desired concentration (not shown).

Diafiltration buffer was also pumped into the reaction vessel at a rate that was controlled so that the total reaction volume remained constant (as in constant-volume-diafiltration), i.e. the rate of introduction of cysteine and diafiltration buffer into the reactor matched the rate of volume loss through the permeate.

Samples were removed at the intervals indicated in the Figures, purified by elution over PD-10 columns, and conjugated with SGD-1269. The conjugated samples were then analyzed by rPLRP. Analysis of the rPLRP chromatograms provided the fraction of heavy chain that remained capped (% H0), the fraction that was selectively reduced at the engineered cysteine (% H1), or the fraction reduced at the engineered cysteine and additionally at an inter-chain disulfide site (% H2; non-selective reduction).

Cysteine Addition Rate Calculation

Cysteine was added to the reaction mixture at the same rate that cysteine is lost through the permeate line. The initial rate of loss of an analyte through the permeate line is calculated from Equation 2, which can be derived from the theoretical equation for clearance by constant volume diafiltration, Equation 1. The rate at which cysteine stock solution is pumped into the reaction mixture to maintain the initial cysteine concentration is then given by Equation 3.

$$C/C_0 = e(-NS).$$ Equation 1:

C is the concentration at any time, t; $C_0$ is the initial concentration; N is the number of diavolumes at time t, and S is the sieving factor for the analyte (determined empirically). The number of diavolumes, N, is $r*t/V_d$, where is r is the permeate flow rate, and $V_d$ is the batch volume. Making this substitution, taking the derivative, and evaluating the derivative at t=0, gives Equation 2.

$$dC/dt = -C_0*(r/V_d)*S,$$ Equation 2:

where dC/dt is the rate of loss of cysteine at $t_0$.

The rate at which cysteine solution must be added to achieve given concentration in the reaction mixture is given by Equation 3.

$$R = -dC/dt*V_d/[Cys],$$ Equation 3:

where [Cys] is the concentration of the cysteine stock solution.

Thus, substituting the expression for dC/dt in Equation 2, gives Equation 4, for the addition rate, $$R = C_0*r*S/[Cys] = (0.8\ \text{mM})*(720\ \text{mL/hr})*(0.8)/(100\ \text{mM}) = 4.61\ \text{mL/hr.}$$ Equation 4:

Results

Figure 2:
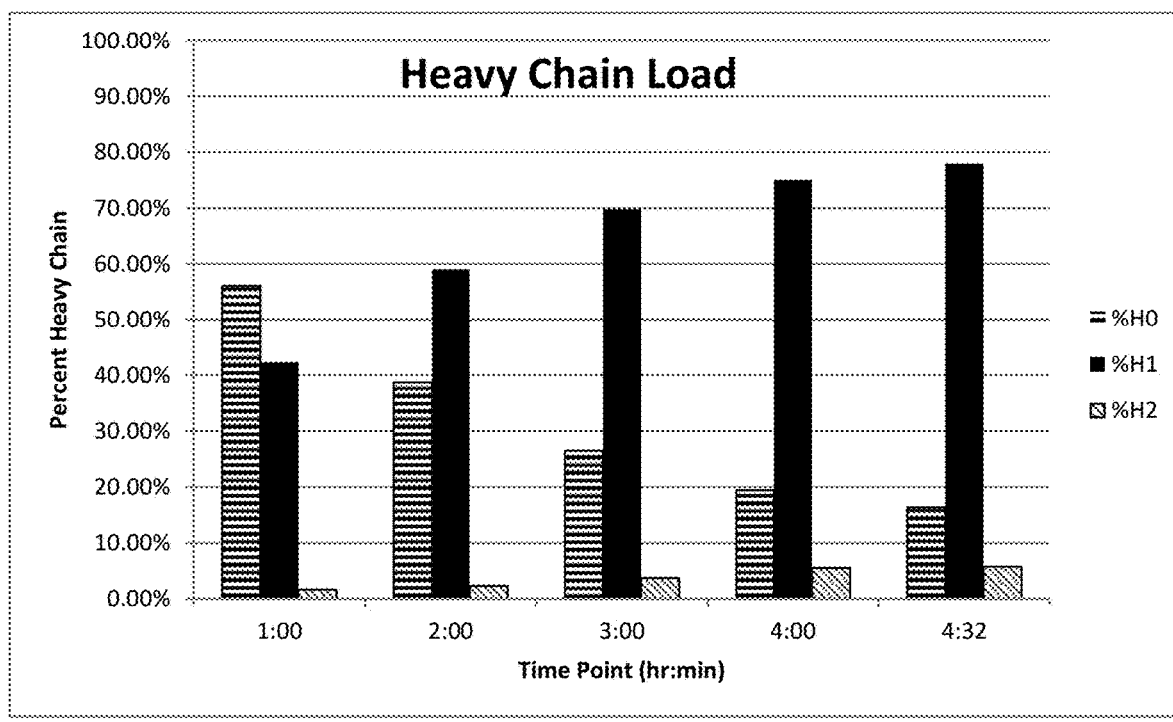
FIG. 2 shows the results of a rPLRP column analysis of heavy chain from a S239C ecmAb mcMMAF ADC. The S239C ecmAb was selectively reduced, by the methods of the invention, and conjugated to the mcMMAF drug-linker. The reducing agent was cysteine at a concentration of 0.8 mM. The activation of the engineered cysteine residues proceeded essentially to completion. Bars marked % H0 indicate heavy chain with no drug-linker conjugated. Bars marked % H1 indicate heavy chain with 1 drug-linker conjugated and bars marked % H2 indicate heavy chain with 2 drug-linkers conjugated.
Figure 3:
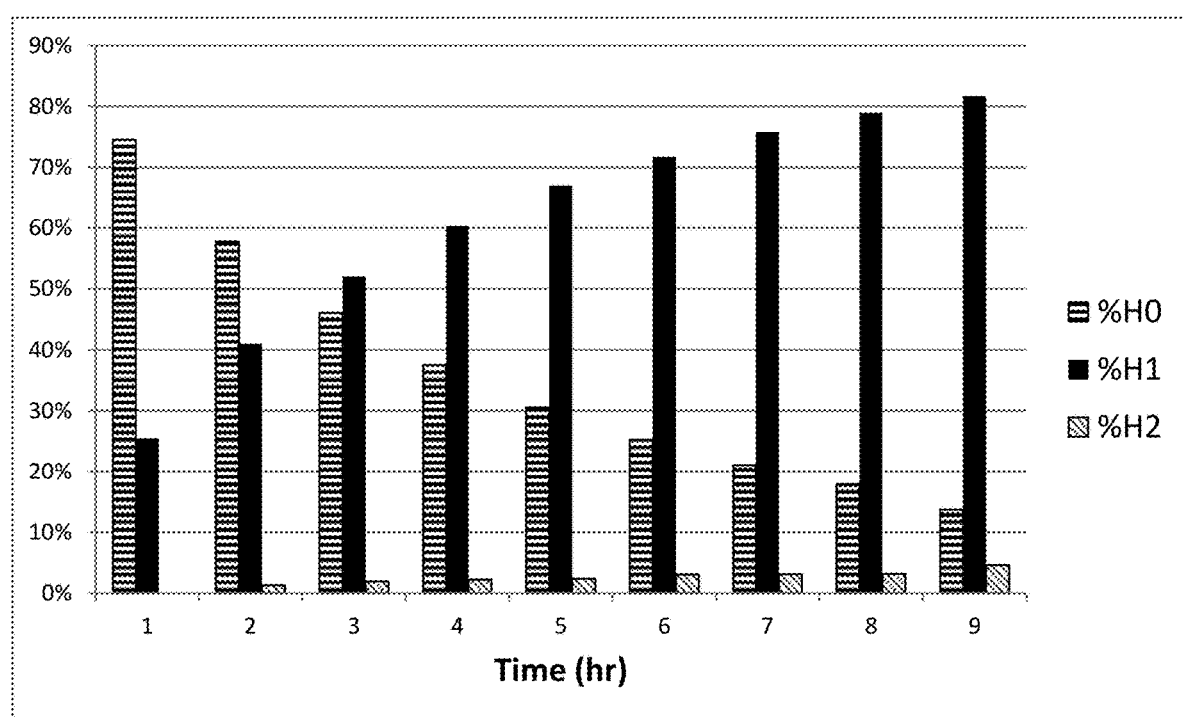
FIG. 3 shows the results of a rPLRP column analysis of heavy chain from a S239C ecmAb mcMMAF ADC. The S239C ecmAb was selectively reduced, by the methods of the invention, and conjugated to the mcMMAF drug-linker. The reducing agent was cysteine at a concentration of 0.55 mM. Only a small percentage of the engineered cysteine residues remained capped (% H0), while the percentage of uncapped engineered cysteine residues approached 100% (% H1), and the amount of non-specific reduction (% H2) remained low.
Figure 4:
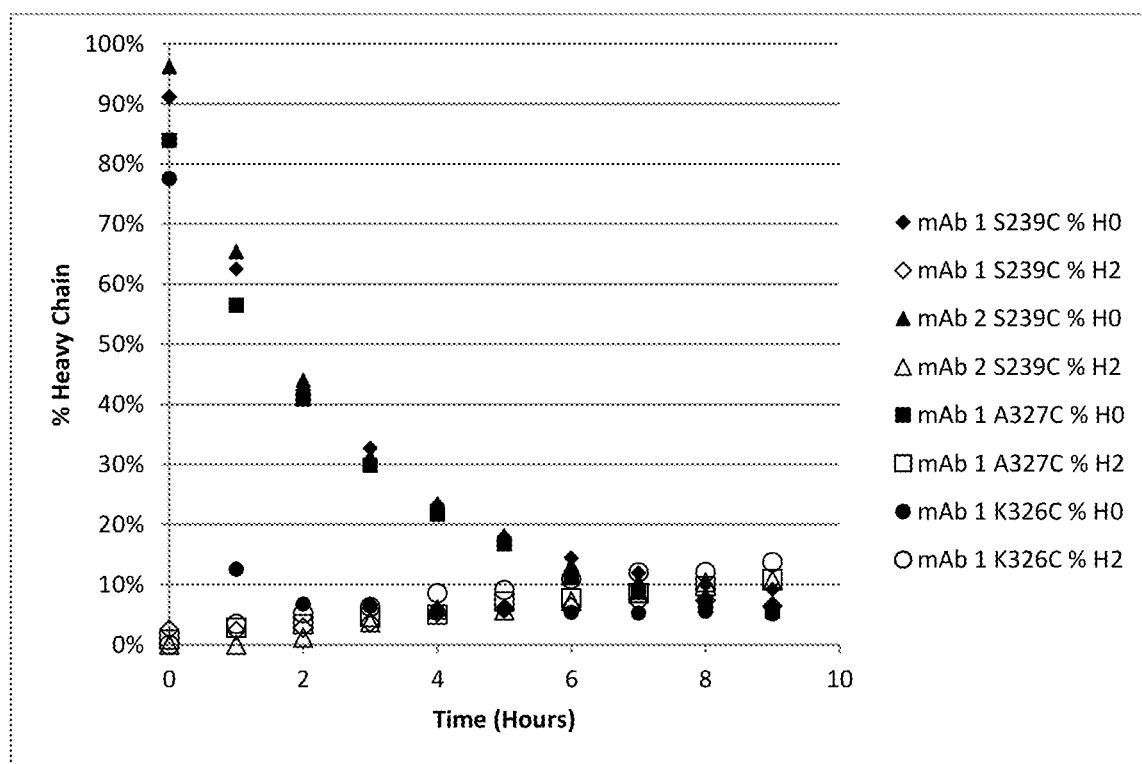
FIG. 4 shows that activation of engineered cysteines was achieved selectively with S239C ecmAbs irrespective of the identity of the heavy and light chain variable regions. mAb1 is the humanized 2H12 ecMAb and mAb2 is the humanized h1F6 ecMab (activation: % H0; selectivity: % H2). The rate of uncapping was similar for the two mAbs. Selective activation of engineered cysteines is demonstrated for mAb1 at 3 different mutation sites, S239, K326 and A327. The results indicate that engineered cysteine activation can be accomplished selectively at a variety of sites. These experiments were performed with ~0.9 mM cysteine.
Figure 5:
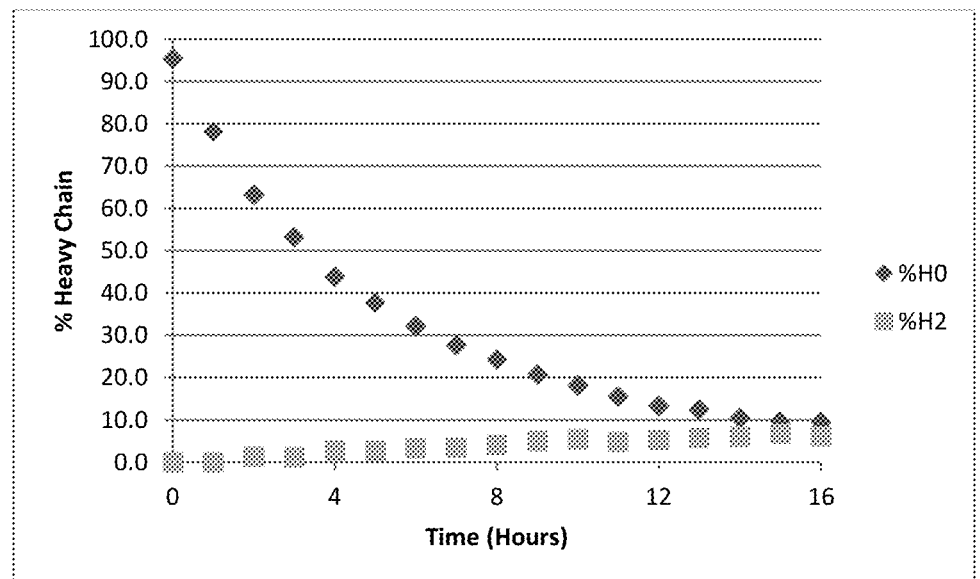
FIG. 5 shows the activation of engineered cysteines for the S239C mutant of mAb1. The mAb concentration in the reaction mixture was approximately the same as for the reactions in FIG. 4, but the cysteine concentration was lower, approximately 0.5 mM throughout the time-course. This experiment showed that maximal selectivity is obtained at a low cysteine concentration, and that given sufficient time, complete activation can be achieved with very good selectivity. The average drug load of the conjugate prepared from the final time point in this experiment was 1.93, which is close to the nominal value of 2.0, and within the range of values obtained by the conventional method of non-selective reduction followed by re-oxidation.

Selective activation of engineered cysteines in the ecmAb was achieved by continuously diafiltering the ecmAb during the reaction, charging cysteine into the diafiltration buffer throughout the process. Diafiltration continuously depleted the reaction byproduct. The cysteine addition rate was calculated based on the theoretical rate of clearance of cysteine by diafiltration, in order to provide a constant concentration of cysteine in the reaction mixture. FIG. 2 shows ~80% activation of available engineered cysteines ("% H1") after 4.5 hr with negligible cleavage of inter-chain disulfide bonds (indicated by % H2). This experiment was repeated using 0.6 mM cysteine, for a longer time, providing a similar result (FIG. 3). At the higher concentration the reaction is faster and somewhat less specific. It will be appreciated that the reaction mixture is in a state of flux throughout the process with cysteine solution entering the reaction mixture through the cysteine feed pump and exiting the reaction mixture through the TFF membrane (permeate), so that the concentration can fluctuate somewhat over the course of the reaction, but nonetheless activation conditions can generally be held close to the nominal concentrations. Cysteine concentrations of 1.5-2 mM and higher resulted in increased inter-chain disulfide cleavage. FIG. 4 demonstrates that engineered cysteine activation can be accomplished selectively at a variety of sites irrespective of the identity of the antibody. The activation time-course the K326 mutant indicates that activation is much faster at this site than at the S239 or A327 sites. This is likely due to the fact that the K326 site is more solvent accessible, but the method achieves the desired selective activation, nonetheless. FIG. 5 illustrates that the reaction can be driven to very close to 100% activation of the engineered cysteines with very good selectivity, by using a low concentration of reducing agent over a long period of time.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A method for selective activation of engineered cysteine residues of engineered cysteine antibodies, said method comprising:
   (a) diafiltering a mixture of engineered cysteine antibodies and buffer, and
   (b) adding a reducing agent to said mixture in a concentration and at a rate to activate a portion of available engineered cysteine residues while retaining at least 80% of all inter-chain disulfide bonds present in the engineered cysteine antibodies prior to (b); and
   (c) maintaining diafiltration of said mixture during step (b);
   to selectively activate the engineered cysteine residues.

2. A method in accordance with claim 1, wherein at least 60% of said engineered cysteine residues are activated.

3. A method in accordance with claim 1, wherein at least 75% of said engineered cysteine residues are activated.

4. A method in accordance with claim 1, wherein less than 20% of said inter-chain disulfide bonds are converted to a pair of free thiols.

5. A method in accordance with claim 1, wherein at least 75% of said engineered cysteine residues are activated, and less than 20% of said inter-chain disulfide bonds are converted to a pair of free thiols.

6. A method in accordance with claim 1, wherein said reducing agent is cysteine.

7. A method in accordance with claim 1, wherein said reducing agent is cysteine, at least 75% of said engineered cysteine residues are activated, and less than 20% of said inter-chain disulfide bonds are converted to a pair of free thiols.

8. A method in accordance with claim 1, wherein at least 80% of inter-chain disulfide bonds present in the engineered cysteine antibodies are retained prior to step (b).

9. A method in accordance with claim 4, wherein less than 15% of said inter-chain disulfide bonds are converted to a pair of free thiols.

10. A method in accordance with claim 9, wherein less than 10% of said inter-chain disulfide bonds are converted to a pair of free thiols.

11. A method in accordance with claim 5, wherein less than 15% of said inter-chain disulfide bonds are converted to a pair of free thiols.

12. A method in accordance with claim 11, wherein less than 10% of said inter-chain disulfide bonds are converted to a pair of free thiols.

13. A method in accordance with claim 7, wherein less than 15% of said inter-chain disulfide bonds are converted to a pair of free thiols.

14. A method in accordance with claim 13, wherein less than 10% of said inter-chain disulfide bonds are converted to a pair of free thiols.

* * * * *